US008173670B2

(12) United States Patent
Xu et al.

(10) Patent No.: US 8,173,670 B2
(45) Date of Patent: May 8, 2012

(54) METHODS OF USING SUBSTITUTED ISOXAZOLO PYRIDINONES AS DISSOCIATED GLUCOCORTICOIDS

(75) Inventors: Huaqiang Eric Xu, Grand Rapids, MI (US); Yong Xu, Grand Rapids, MI (US); Yuanzheng He, Grand Rapids, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 0 days.

(21) Appl. No.: 12/686,805

(22) Filed: Jan. 13, 2010

(65) Prior Publication Data
US 2011/0251211 A9 Oct. 13, 2011

Related U.S. Application Data

(60) Provisional application No. 61/144,326, filed on Jan. 13, 2009.

(51) Int. Cl.
*A01N 43/42* (2006.01)
(52) U.S. Cl. .................................. 514/302
(58) Field of Classification Search .............. None
See application file for complete search history.

(56) References Cited

U.S. PATENT DOCUMENTS

| 4,049,813 | A | 9/1977 | Nadelson |
| 4,086,421 | A | 4/1978 | Nadelson |
| 7,087,756 | B2 | 8/2006 | Hintermann et al. |

FOREIGN PATENT DOCUMENTS

| EP | 1408042 A1 | 4/2004 |

OTHER PUBLICATIONS

Vippagunta et al., Advanced Drug Delivery Reviews, 48, pp. 3-26, (2001).*
Hintermann, S. et al., Identification of a series of highly potent activators of the Nurr1 signaling pathway. Bioorganic & Medicinal Chemistry Letters, 17: 193-196 (2007).
De Bosscher K, et al., "The Interplay Between the Glucocorticoid Receptor and Nuclear Factor-kB or Activator Protein-1: Molecular Mechanisms for Gene Repression". Endocrine Reviews, vol. 24 (4): 488-522 (Aug. 2003).
De Bosscher K, et al., "Minireview: Latest Perspectives on Antiinflammatory Actions of Glucocorticoids". Mol Endocrinol, vol. 23(3): 281-291 (Mar. 2009).
Suino-Powell, K. et al.,"Doubling the Size of the Glucocorticoid Receptor Ligand Binding Pocket by Deacylcortivazol", Molecular and Cellular Biology, vol. 28 (6): 1915-1923 (Mar. 2008).
Tait, S.A. et al., "The Role of Glucocorticoids and Progestins in Inflammatory, Autoimmune, and Infectious Disease", Journal of Leukocyte Biology, vol. 84 (4): 924-931 (Oct. 2008).
Alangari, Abdullah A. et al., Genomic and Non-genomic Actions of Glucocorticoids in Asthma, Annals of Thoracic Medicine, vol. 5, Issue 3, pp. 133-139, Jul.-Sep. 2010.
Reither, Doris et al., Nonsteroidal Dissociated Glucocoticoid Agonists Containing Azaindoles as Steroid A-Ring Mimetics, Journal of Medicinal Chemistry, vol. 53, Issue 18, pp. 6681-6698, Aug. 24, 2010.
International Search Report, PCT/US2010/020901, Mar. 18, 2010.
Written Opinion, PCT/US2010/020901, Jul. 13, 2011.

* cited by examiner

*Primary Examiner* — Sreeni Padmanabhan
*Assistant Examiner* — Svetlana M Ivanova
(74) *Attorney, Agent, or Firm* — Honigman Miller Schwartz and Cohn LLP; Douglas H. Siegel

(57) ABSTRACT

A method for treating a subject having an inflammatory or auto-immune disease with a substituted isoxazolo pyridinone. Also, a method for administering a substituted isoxazolo pyridinone to a cell to retain or increase glucocorticoid receptor transrepression activity with only minimal glucocorticoid receptor transactivation activity.

9 Claims, 10 Drawing Sheets

METHODS OF USING SUBSTITUTED ISOXAZOLO PYRIDINONES AS DISSOCIATED GLUCOCORTICOIDS

This application claims benefit of provisional application Ser. No. 61/144,326, filed Jan. 13, 2009, entitled Methods of Using Substituted Isoxazolo Pyridinones as Dissociated Glucocorticoids, the entire contents of which are incorporated herein in their entirety.

STATEMENT REGARDING FEDERALLY SPONSORED RESEARCH OR DEVELOPMENT

This invention was made with government support under DK 071662 awarded by the National Institute of Health. The government has certain rights in the invention.

BACKGROUND OF THE INVENTION

The glucocorticoid receptor (GR) is a steroid hormone receptor which belongs to the nuclear receptor superfamily (nuclear receptor subfamily 3, group C, member 1). GR is encoded by gene NR3C1 on chromosome 5 (5q31). GR plays an important role in many physiologic processes, such as regulating glucose and lipid metabolism, bone development, and maintaining body salt balance.

GR exerts its physiologic roles through binding to its ligand (e.g. corticoid). The activated form of GR has two principal mechanisms of action: transactivation and transrepression of target gene expression. "Transactivation" is a direct mechanism of action involves homodimerization of GR, translocation via active transport into the nucleus, and binding to specific DNA responsive elements, thereby activating gene transcription. In transrepression, GR does not directly bind to target DNA, instead, GR is tethered to other transcriptional factors, such as NF-kB or AP-1, by protein-protein interaction, thereby repressing the transcriptional activity of the tethered transcriptional factors, e.g., NF-kB transcriptional activity on IL-6, IFN-b, ICAM1 etc genes.

GR is a target for treating anti-inflammatory and self-immune diseases, such as rheumatoid arthritis, asthma, allograft rejection, and allergic skin diseases. Treatment is based on the transrepression properties of GR on major proinflammatory cytokines, such as TNF-alpha, IL-8, IL-6 and IL-1 beta. GR also has transrepression properties with respect to NF-kB. NF-kB is not a proinflammatory cytokine, but is a master regulator of proinflammatory cytokines, i.e., it can induce many proinflammatory cytokines, such as IL-1b, IL-6, IL-8, IFN-b. Usually the activation of NF-kB occurs at the onset of inflammation.

GR also is an important target for treating leukemia, especially Childhood Acute Lymphoblastic Leukemia (ALL). This treatment is based on inducing apoptosis in leukemia cells with a corticoid-like GR agonist, such as dexamethasone (DEX).

Unfortunately, corticoid-like drugs can result in side effects because of the unwanted transactivation activity of GR. As such, long term use of corticoid-like drugs can lead to diabetes, osteoporosis, skin atrophy, and growth retardation. Thus, an important issue for corticoid-like anti-inflammatory drug discovery is to identify a GR ligand which can retain or increase GR transrepression activity, but with only minimal remaining GR transactivation activity. Such a GR ligand is called a "dissociated GR ligand". However, all of the known attempts to identify a dissociated GR ligand have resulted in a GR ligand that either (a) retains only a very small part of its transrepression activity, or (b) has significant transactivation activity, e.g., undesirable side effects. As such, none of these known compounds has been used in a clinical setting to date.

BRIEF SUMMARY OF THE INVENTION

The present invention includes a method of treating a disease selected from the group consisting of arthritis, asthma, lupus, allograft rejection, allergic skin disease, leukemia, multiple sclerosis, inflammatory liver disease, autoimmune hepatitis, inflammatory bowel disease, metabolic disorders, atherosclerosis, brain edema, shock, blood cancer, and adrenal cortex insufficiencies in useful warm blooded mammals which comprises administering a therapeutically effective amount of an isoxazolo[4,5-c]pyridine of formula (I)

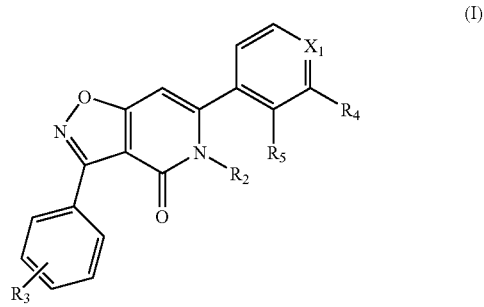

(I)

where:
- $X_1$ is —N= and —$CR_1$=;
- $R_1$ is —H,
  - $C_1$-$C_3$ alkyl,
  - —$(CH_2)_x$—N($R_{1-1}$)($R_{1-2}$) where x is 0, 1 or 2 and where $R_{1-1}$ and $R_{1-2}$ are the same or different and are —H and $C_1$-$C_3$ alkyl with the proviso that when $R_{1-1}$ and $R_{1-2}$ are both $C_2$ alkyl, the alkyl groups can be cyclized to form a heterocyclic ring selected from the group consisting of pyrrolidinyl, piperidinyl, piperizinyl and N-methylpiperazinyl;
  - —O—$R_{1-3}$ where $R_{1-3}$ is —H, $C_1$-$C_3$ alkyl and phenyl;
  - —$(CH)_y$—O—$(CH_2)_y$—O—$R_{1-4}$ where y are the same or different and are 1 or 2 and where $R_{1-4}$ is —H, $C_1$-$C_3$ alkyl, —CO—$R_{1-5}$ where $R_{1-5}$ is $C_1$-$C_4$ and phenyl;
- $R_2$ is —H, $C_1$-$C_3$ alkyl, and $C_3$ cycloalkyl;
- $R_3$ is —H, $C_1$-$C_3$ alkyl, —F, —Cl, —Br and —I;
- $R_4$ is —H and —O—$R_{4-1}$ with the proviso that when $R_4$ is —O—$R_{4-1}$, $X_1$ is —$R_1$= and $R_1$ and $R_4$ are taken together to form a methylenedioxo group;
- $R_5$ is —H and —O—$R_{5-1}$ where $R_{5-1}$ is —H, $C_1$-$C_3$ alkyl and phenyl with the proviso that $R_{5-1}$ and $R_{1-3}$ cannot both be phenyl; enantiomers, diastereomers, tautomers, pharmaceutically acceptable salts and hydrates thereof.

With the present method of treating a disease: the disease treated may be arthritis, asthma, lupus, allograft rejection, allergic skin disease and leukemia; the useful warm blooded mammal may be a human; the effective amount may be from about 1 to about 100 mg/kg/day or from about 5 to about 50 mg/kg/day; R2 may be C1 alkyl; or R3 may be —H or —F.

Further, with the present method of treating a disease the isoxazolo[4,5-c]pyridine (I) may be: 6-(4-((dimethylamino)methyl)phenyl)-5-methyl-3phenylisoxazolo[4,5-c]pyridin-4(5H)-one; 6-(4-((dimethylamino)methyl)phenyl)-3-(4-fluorophenyl)-5methylisoxazolo[4,5-c]pyridin-4(5H)-one; 6-(4-diethylamino-phenyl)-5-methyl-3-phenyl-5H-isoxazolo[4,5c]pyridin-4-one; 6-(4-methoxyphenyl)-5-methyl-3-phenylisoxazolo[4,5-c]pyridin-4(5H)-one; 6-(2,4- dimethoxyphenyl)-5-methyl-3-phenylisoxazolo[4,5-c]
pyridin-4(5H)-one; 6-(benzo[d][1,3]dioxol-5-yl)-5-methyl-
3-phenylisoxazolo[4,5c]pyridin-4(5H)-one; 6-(4-((2-
hydroxyethoxy)methyl)phenyl)-5-methyl-3phenylisoxazolo
[4,5-c]pyridin-4(5H)-one; 6-(4-((2-methoxyethoxy)methyl)
phenyl)-5-methyl-3phenylisoxazolo[4,5-c]pyridin-4(5H)-
one; 6-(4-((2-isopropoxyethoxy)methyl)phenyl)-5-methyl-
3phenylisoxazolo[4,5-c]pyridin-4(5H)-one; 5-methyl-6-(4-
phenoxyphenyl)-3-phenyl-isoxazolo[4,5-c]pyridin-4(5H)-
one; 5-methyl-6-(4-((4-methylpiperazin-1-yl)methyl)
phenyl)-3phenylisoxazolo[4,5-c]pyridin-4(5H)-one;
5-methyl-3-phenyl-6-(pyridin-4-yl)isoxazolo[4,5-c]pyridin-
4(5H)-one; or 5-methyl-3-phenyl-6-p-tolylisoxazolo[4,5-c]
pyridin-4(5H)-one. In one embodiment, the isoxazolo[4,5-c]
pyridine (I) may be 6-(4-((dimethylamino)methyl)phenyl)-5-
methyl-3phenylisoxazolo[4,5-c]pyridin-4(5H)-one.

The present invention also includes a method for retaining
or increasing glucocorticoid receptor transrepression activity
in a cell with only minimal glucocorticoid receptor transac-
tivation activity comprising administering to a cell which
needs modification a usable amount of an isoxazolo[4,5-c]
pyridine of formula (I) as described herein; enantiomers,
diastereomers, tautomers, pharmaceutically acceptable salts
and hydrates thereof.

Further, with the present method for retaining or increasing
glucocorticoid receptor transrepression activity in a cell with
only minimal glucocorticoid receptor transactivation activity,
the isoxazolo[4,5-c]pyridine (I) may be: 6-(4-((dimethy-
lamino)methyl)phenyl)-5-methyl-3phenylisoxazolo[4,5-c]
pyridin-4(5H)-one; 6-(4-((dimethylamino)methyl)phenyl)-
3-(4-fluorophenyl)-5methylisoxazolo[4,5-c]pyridin-4(5H)-
one; 6-(4-diethylamino-phenyl)-5-methyl-3-phenyl-5H-
isoxazolo[4,5c]pyridin-4-one; 6-(4-methoxyphenyl)-5-
methyl-3-phenylisoxazolo[4,5-c]pyridin-4(5H)-one; 6-(2,4-
dimethoxyphenyl)-5-methyl-3-phenylisoxazolo[4,5-c]
pyridin-4(5H)-one; 6-(benzo[d][1,3]dioxol-5-yl)-5-methyl-
3-phenylisoxazolo[4,5c]pyridin-4(5H)-one; 6-(4-((2-
hydroxyethoxy)methyl)phenyl)-5-methyl-3phenylisoxazolo
[4,5-c]pyridin-4(5H)-one; 6-(4-((2-methoxyethoxy)methyl)
phenyl)-5-methyl-3phenylisoxazolo[4,5-c]pyridin-4(5H)-
one; 6-(4-((2-isopropoxyethoxy)methyl)phenyl)-5-methyl-
3phenylisoxazolo[4,5-c]pyridin-4(5H)-one; 5-methyl-6-(4-
phenoxyphenyl)-3-phenyl-isoxazolo[4,5-c]pyridin-4(5H)-
one; 5-methyl-6-(4-((4-methylpiperazin-1-yl)methyl)
phenyl)-3phenylisoxazolo[4,5-c]pyridin-4(5H)-one;
5-methyl-3-phenyl-6-(pyridin-4-yl)isoxazolo[4,5-c]pyridin-
4(5H)-one; or 5-methyl-3-phenyl-6-p-tolylisoxazolo[4,5-c]
pyridin-4(5H)-one. In one embodiment, the isoxazolo[4,5-c]
pyridine (I) may be 6-(4-((dimethylamino)methyl)phenyl)-5-
methyl-3phenylisoxazolo[4,5-c]pyridin-4(5H)-one. In
another embodiment, R2 may be C1 alkyl or R3 may be —H
or —F.

BRIEF DESCRIPTION OF THE DRAWINGS

The foregoing summary, as well as the following detailed
description of the invention, will be better understood when
read in conjunction with the appended drawings. For the
purpose of illustrating the invention, there are shown in the
drawings, certain embodiment(s) which are presently pre-
ferred. It should be understood, however, that the invention is
not limited to the precise arrangements and instrumentalities
shown.

Figure 1:
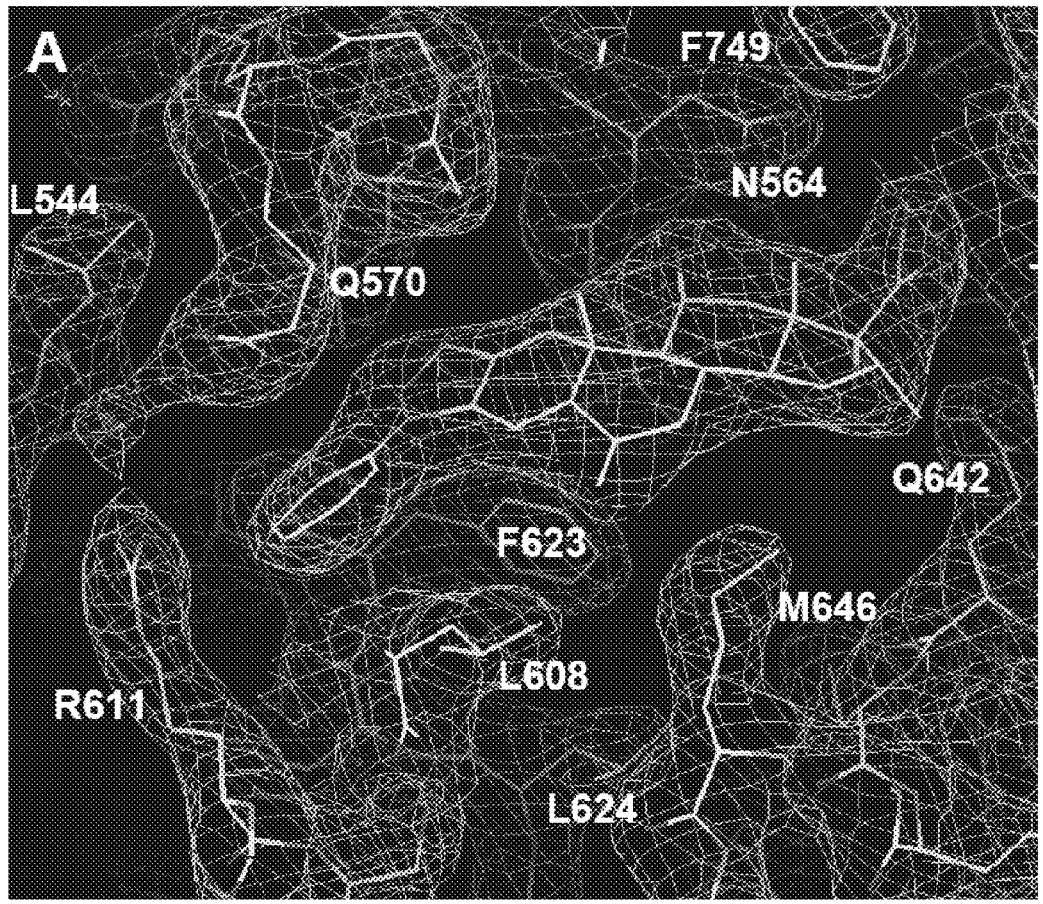
FIG. 1 shows the crystal structure of DAC bound in the GR
LBD (3BQD.pdb).

DETAILED DESCRIPTION OF THE PREFERRED
EMBODIMENTS

Before the subject invention is described further, it is to be
understood that the invention is not limited to the particular
embodiments of the invention described below, as variations
of the particular embodiments may be made and still fall
within the scope of the appended claims. It is also to be
understood that the terminology employed is for the purpose
of describing particular embodiments, and is not intended to
be limiting. Instead, the scope of the present invention will be
established by the appended claims.

Where a range of values is provided, it is understood that
each intervening value, to the tenth of the unit of the lower
limit unless the context clearly dictates otherwise, between
the upper and lower limit of that range, and any other stated or
intervening value in that stated range, is encompassed within
the invention. The upper and lower limits of these smaller
ranges may independently be included in the smaller ranges,
and are also encompassed within the invention, subject to any
specifically excluded limit in the stated range. Where the
stated range includes one or both of the limits, ranges exclud-
ing either or both of those included limits are also included in
the invention.

All references, patents, patent publications, articles, and
databases, referred to in this application are incorporated
herein by reference in their entirety, as if each were specifi-
cally and individually incorporated herein by reference. Such
patents, patent publications, articles, and databases are incor-
porated for the purpose of describing and disclosing the sub-
ject components of the invention that are described in those
patents, patent publications, articles, and databases, which
components might be used in connection with the presently
described invention. The information provided below is not
admitted to be prior art to the present invention, but is pro-
vided solely to assist the understanding of the reader.

The details of one or more embodiments of the invention
are set forth in the accompanying drawings and the descrip-
tion below. Other features, embodiments, and advantages of
the invention will be apparent from the description and draw-
ings, and from the claims. The preferred embodiments of the
present invention may be understood more readily by refer-
ence to the following detailed description of the specific
embodiments and the Examples included hereafter.

For clarity of disclosure, and not by way of limitation, the
detailed description of the invention is divided into the sub-
sections that follow.

Unless defined otherwise, all technical and scientific terms
used herein have the meaning commonly understood by one of ordinary skill in the art to which this invention belongs. Generally, the nomenclature used herein and the laboratory procedures in cell culture, molecular genetics, organic chemistry and nucleic acid chemistry described below are those well known and commonly employed in the art. Although any methods, devices and materials similar or equivalent to those described herein can be used in the practice or testing of the invention, the preferred methods, devices and materials are now described.

In this specification and the appended claims, the singular forms "a," "an" and "the" include plural reference unless the context clearly dictates otherwise.

When the term "Cx-Cy alkyl" is used, it means an alkyl group beginning with Cx including and thru Cy including isomers thereof where such exist but does not include cyclic forms. Therefore, "C1-C3 alkyl" includes methyl, ethyl, n-propyl and i-propyl.

Figure 2:
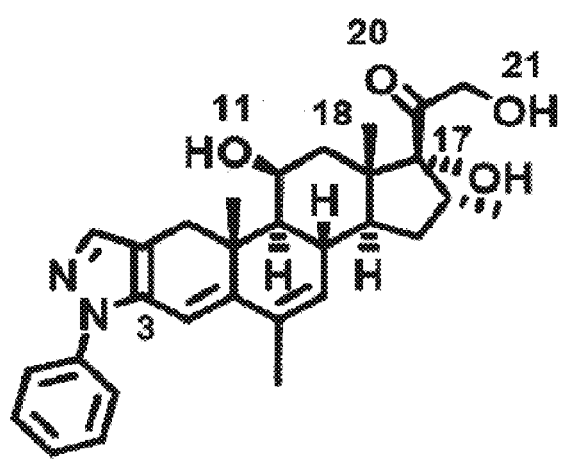
FIG. 2 shows the 2-dimensional chemical structure of
DAC.

One or more of the Applicants has recently determined the crystal structure of GR bound to deacylcortivazol (DAC), a potent glucocorticoid. Suino-Powell, K., et. al, *Molecular and Cellular Biology*, Vol. 28, No. 6, 1915-1923 (March 2008). The GR-DAC structure reveals an expanded GR DAC-binding pocket that is twice the size of the GR DEX-binding pocket (FIG. 1). FIG. 2 shows the 2-dimensional chemical structure of DAC.

By screening public chemical data banks for molecules that would fit the expanded binding pocket, and through molecular docking studies, the inventors identified a class of compounds that have the ability to bind to GR similar to the ability of DAC to bind to GR. This class includes isoxazolo[4,5-c]pyridines of formula (I)

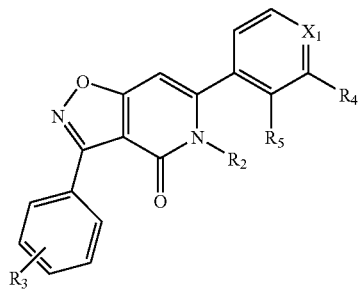

(I)

where:
  $X_1$ is —N= and —$CR_1$=;
  $R_1$ is —H,
  $C_1$-$C_3$ alkyl,
  —$(CH_2)_x$—$N(R_{1-1})(R_{1-2})$ where x is 0, 1 or 2 and where $R_{1-1}$ and $R_{1-2}$ are the same or different and are —H and $C_1$-$C_3$ alkyl with the proviso that when $R_{1-1}$ and $R_{1-2}$ are both $C_2$ alkyl, the alkyl groups can be cyclized to form a heterocyclic ring selected from the group consisting of pyrrolidinyl, piperidinyl, piperizinyl and N-methylpiperazinyl;
  —O—$R_{1-3}$ where $R_{1-3}$ is —H, $C_1$-$C_3$ alkyl and phenyl;
  —$(CH)_y$—O—$(CH_2)_y$—O—$R_{1-4}$ where y are the same or different and are 1 or 2 and where $R_{1-4}$ is —H, $C_1$-$C_3$ alkyl, —CO—$R_{1-5}$ where $R_{1-5}$ is $C_1$-$C_4$ and phenyl;
  $R_2$ is —H, $C_1$-$C_3$ alkyl, and $C_3$ cycloalkyl;
  $R_3$ is —H, $C_1$-$C_3$ alkyl, —F, —Cl, —Br and —I;
  $R_4$ is —H and —O—$R_{4-1}$ with the proviso that when $R_4$ is —O—$R_{4-1}$, $X_1$ is —$R_1$= and $R_1$ and $R_4$ are taken together to form a methylenedioxo group;
  $R_5$ is —H and —O—$R_{5-1}$, where $R_{5-1}$ is —H, $C_1$-$C_3$ alkyl and phenyl with the proviso that $R_{5-1}$ and $R_{1-3}$ cannot both be phenyl; enantiomers, diastereomers, tautomers, pharmaceutically acceptable salts and hydrates thereof.

Through GR transrepression and GR transactivation studies, the inventors found that the class of compounds of formula I has dissociated GR ligand properties. Thus, the present invention includes a method for retaining or increasing glucocorticoid receptor transrepression activity with only minimal glucocorticoid receptor transactivation activity in a cell comprising administering to a cell which needs modification a usable amount of the compound of formula I,

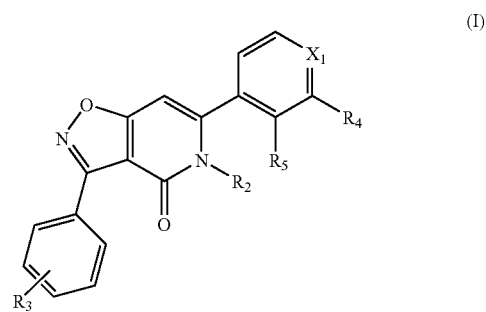

(I)

where:
  $X_1$ is —N= and —$CR_1$=;
  $R_1$ is —H,
  $C_1$-$C_3$ alkyl,
  —$(CH_2)_x$—$N(R_{1-1})(R_{1-2})$ where x is 0, 1 or 2 and where $R_{1-1}$ and $R_{1-2}$ are the same or different and are —H and $C_1$-$C_3$ alkyl with the proviso that when $R_{1-1}$ and $R_{1-2}$ are both $C_2$ alkyl, the alkyl groups can be cyclized to form a heterocyclic ring selected from the group consisting of pyrrolidinyl, piperidinyl, piperizinyl and N-methylpiperazinyl;
  —O—$R_{1-3}$ where $R_{1-3}$ is —H, $C_1$-$C_3$ alkyl and phenyl;
  —$(CH)_y$—O—$(CH_2)_y$—O—$R_{1-4}$ where y are the same or different and are 1 or 2 and where $R_{1-4}$ is —H, $C_1$-$C_3$ alkyl, —CO—$R_{1-5}$ where $R_{1-5}$ is $C_1$-$C_4$ and phenyl;
  $R_2$ is —H, $C_1$-$C_3$ alkyl, and $C_3$ cycloalkyl;
  $R_3$ is —H, $C_1$-$C_3$ alkyl, —F, —Cl, —Br and —I;
  $R_4$ is —H and —O—$R_{4-1}$ with the proviso that when $R_4$ is —O—$R_{4-1}$, $X_1$ is —$R_1$= and $R_1$ and $R_4$ are taken together to form a methylenedioxo group;
  $R_5$ is —H and —O—$R_{5-1}$ where $R_{5-1}$ is —H, $C_1$-$C_3$ alkyl and phenyl with the proviso that $R_{5-1}$ and $R_{1-3}$ cannot both be phenyl; its enantiomers, diastereomers, tautomers, pharmaceutically acceptable salts and hydrates thereof. In one embodiment, the administered compound is 6-(4-((dimethylamino)methyl)phenyl)-5-methyl-3-phenylisoxazolo[4,5-c]pyridin-4(5H)-one [this compound is known as "Compound #53]. The isoxazolopyridinones of formula (I) are known to those skilled in the art or can be readily prepared by one skilled in the art by known means from compounds known to those skilled in the art. The isoxazolopyridinones (I) of Examples 5-17 are known to those skilled in the art.

By "a usable amount" herein is meant an amount of the isoxazolo[4,5-c]pyridine of formula (I) that produces the effect for which it is administered to a cell. For example, a usable amount of the isoxazolo[4,5-c]pyridine of formula (I) is that amount of the isoxazolo[4,5-c]pyridine of formula (I) that retains or increases glucocorticoid receptor transrepression activity in a cell with only minimal glucocorticoid receptor transactivation activity. The selected compound of formula I is given in an amount to retain or increase glucocorticoid receptor transrepression activity in a cell with only minimal glucocorticoid receptor transactivation activity, which amount is from about 1 µM to about 50 µM, or from about 5 µM to about 10 µM.

As used herein, the term "retaining or increasing glucocorticoid receptor transrepression activity" or "retains or increases glucocorticoid receptor transrepression activity" means the same or an increase in glucocorticoid receptor transrepression activity in a cell as compared to the glucocorticoid receptor transrepression activity in a cell caused by the administration of a standard GR ligand, such as Dexamethasone.

As used herein, the term "minimal glucocorticoid receptor transactivation activity" means glucocorticoid receptor transactivation activity that is <15% of the glucocorticoid receptor transactivation activity caused by the administration of Dexamethasone to a cell. The minimal glucocorticoid receptor transactivation activity also may be glucocorticoid receptor transactivation activity that is 20%, 30%, 40%, 50%, 60, 70%, 80%, or 90% of the glucocorticoid receptor transactivation activity caused by the administration of Dexamethasone to a cell.

Figure 3:
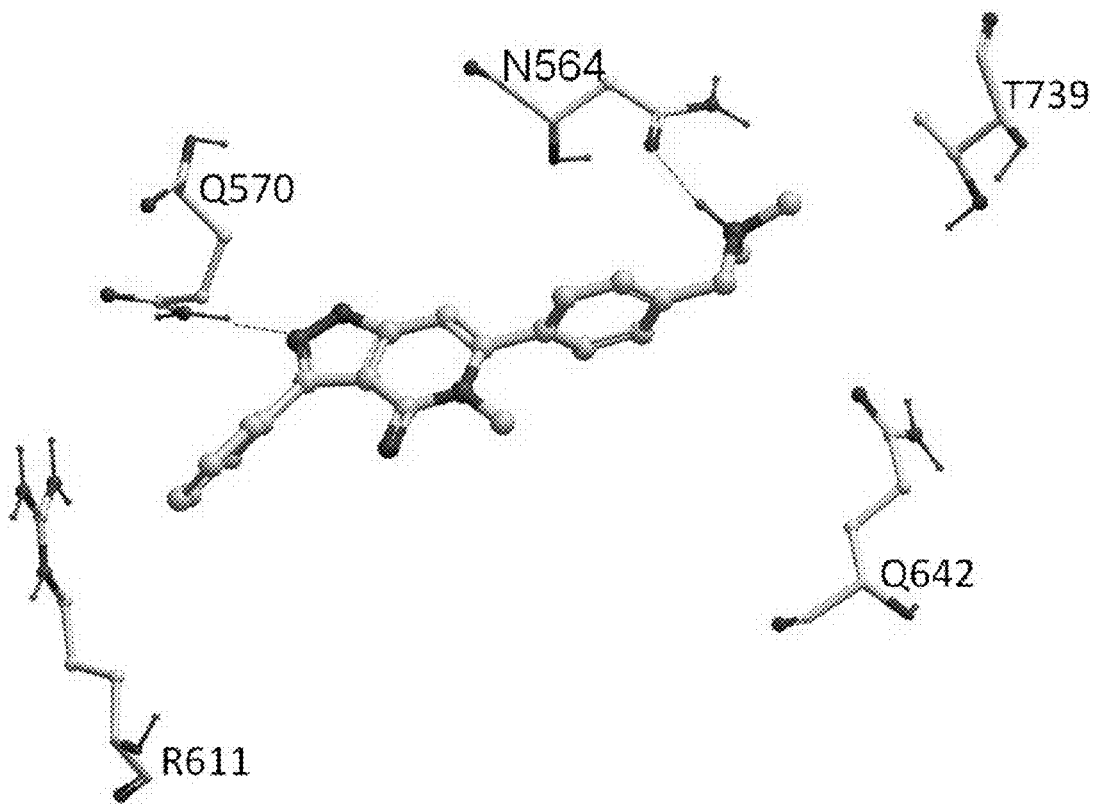
FIG. 3 shows the structure of Compound #53 bound in the
GR LBD as predicted by the molecular docking program
GOLD.
Figure 4:
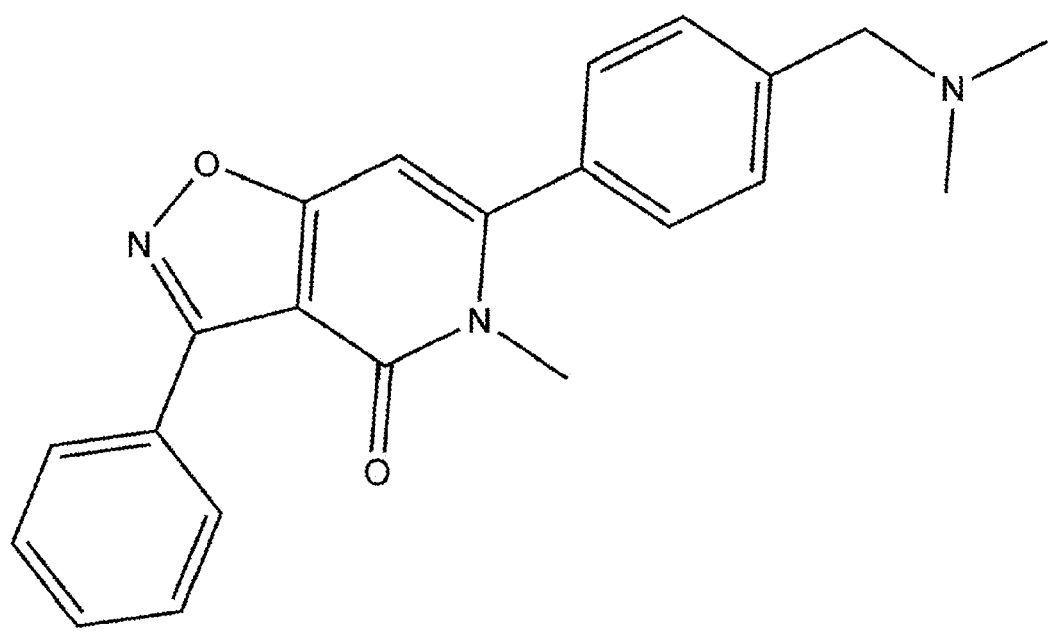
FIG. 4 shows the 2-dimensional chemical structure of
Compound #53.
Figure 5:
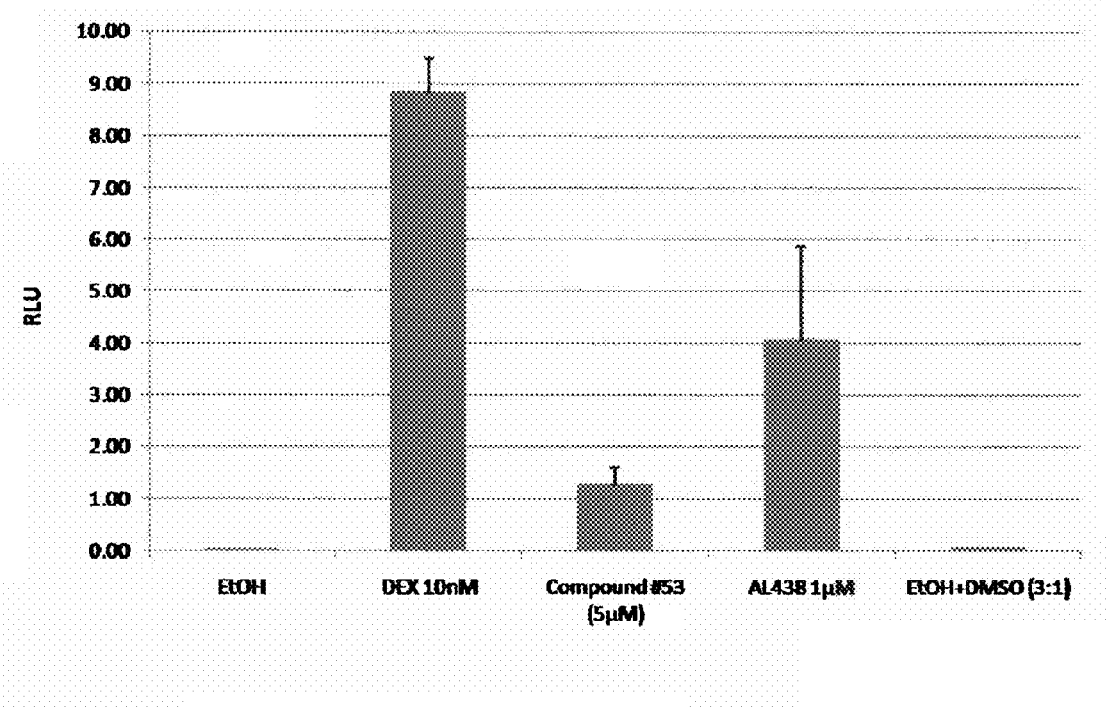
FIG. 5 is a bar graph showing Compound #53's transacti-
vation activity on MMTV in AD293 cells
Figure 6:
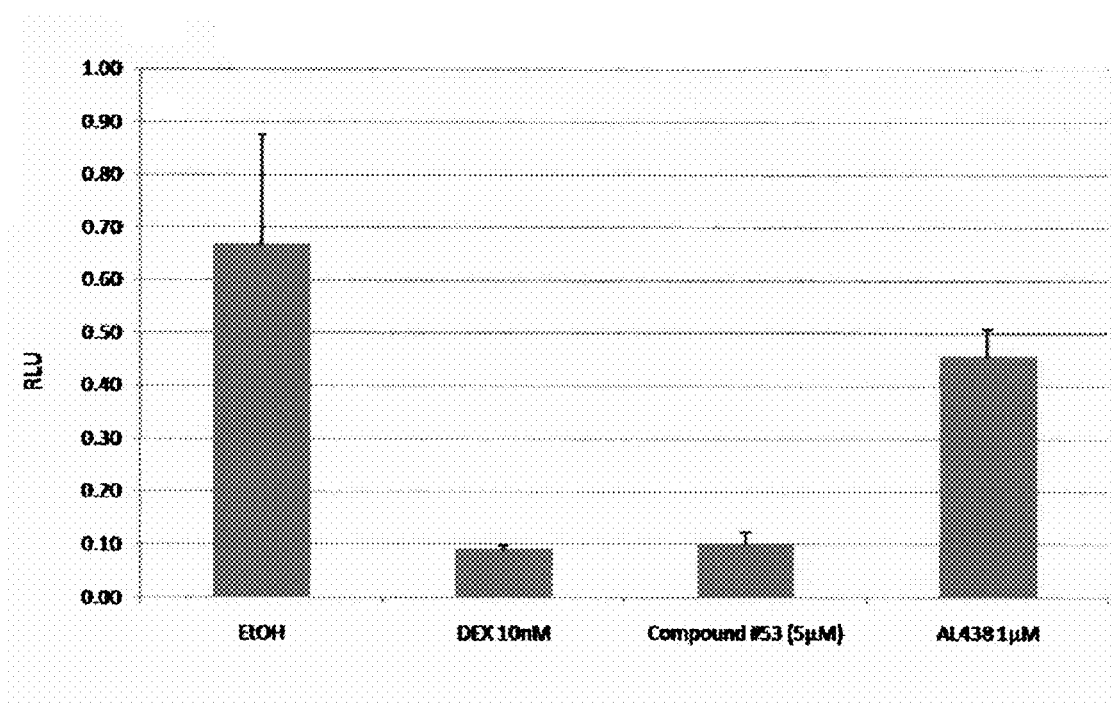
FIG. 6 is a bar graph showing Compound #53's GR tran-
srepression activity on AP1 in AD293 cells.
Figure 7:
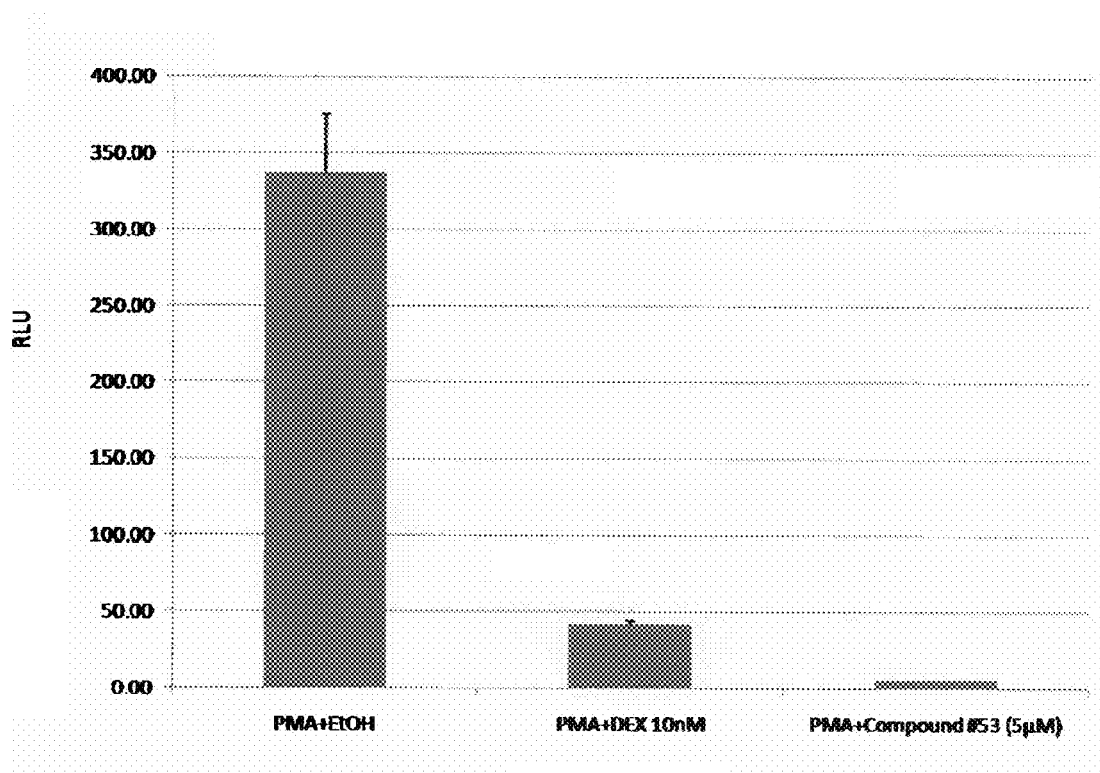
FIG. 7 is a bar graph showing Compound #53's GR tran-
srepression activity on AP1 in AD293 cells.
Figure 8:
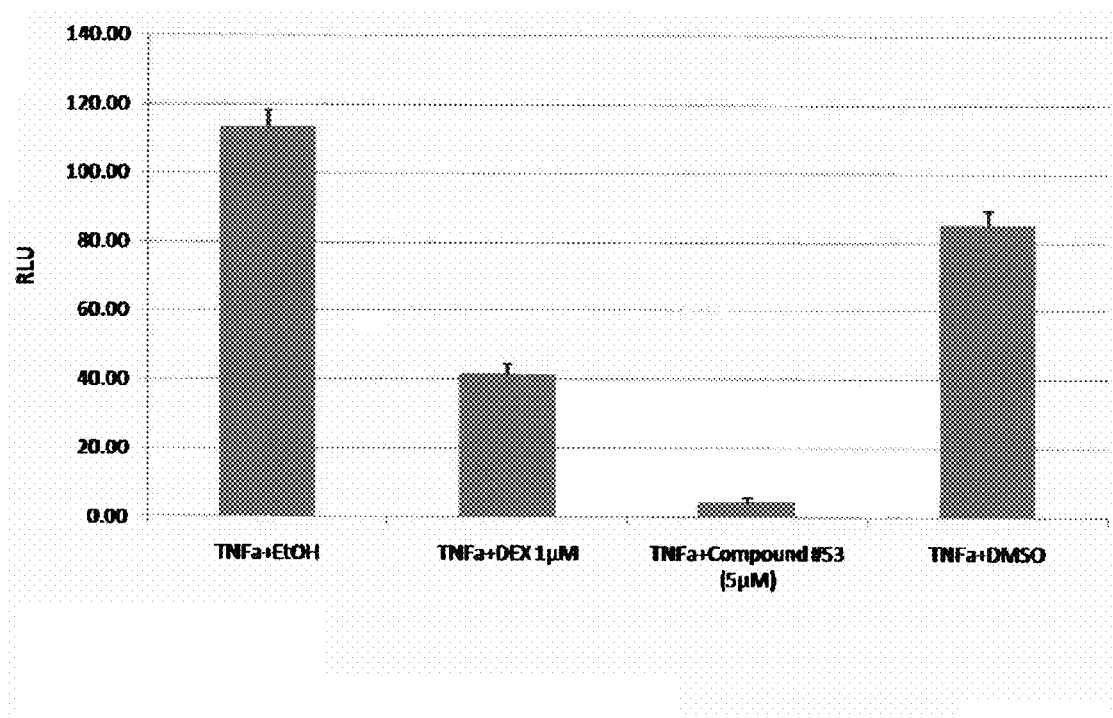
FIG. 8 is a bar graph showing Compound #53's GR tran-
srepression activity on NF-kB in AD293 cells.
Figure 9:
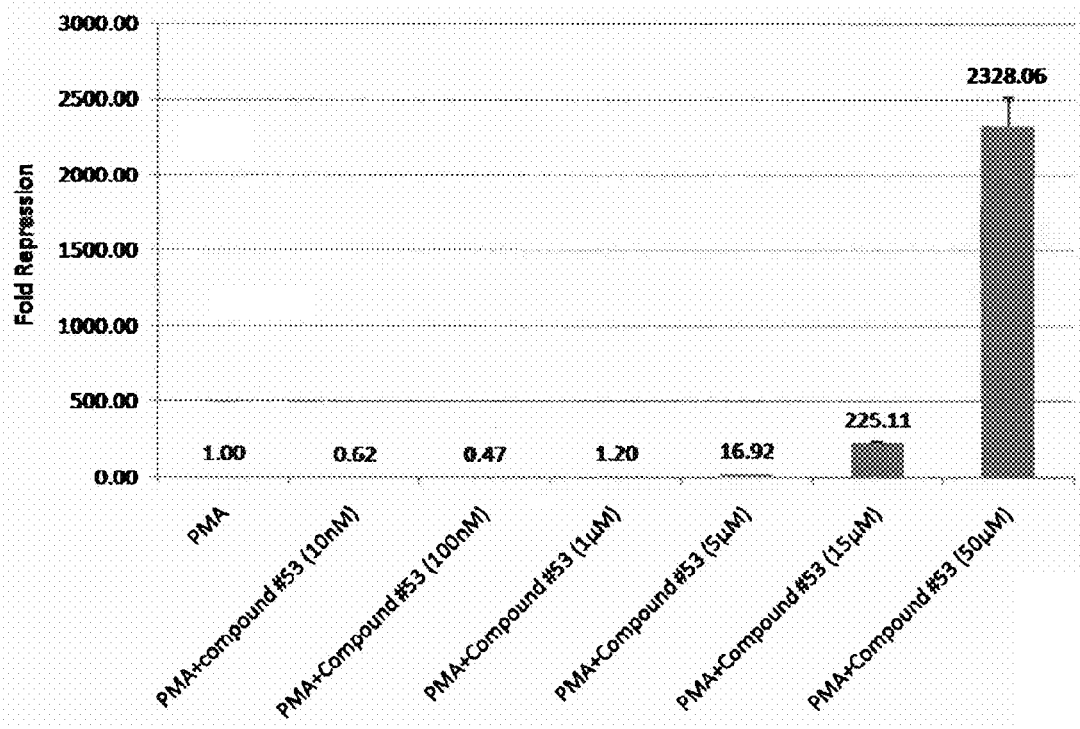
FIG. 9 is a bar graph showing the dose-response of Com-
pound #53 on GR transrepression of AP1 in AD293 cells.
Figure 10:
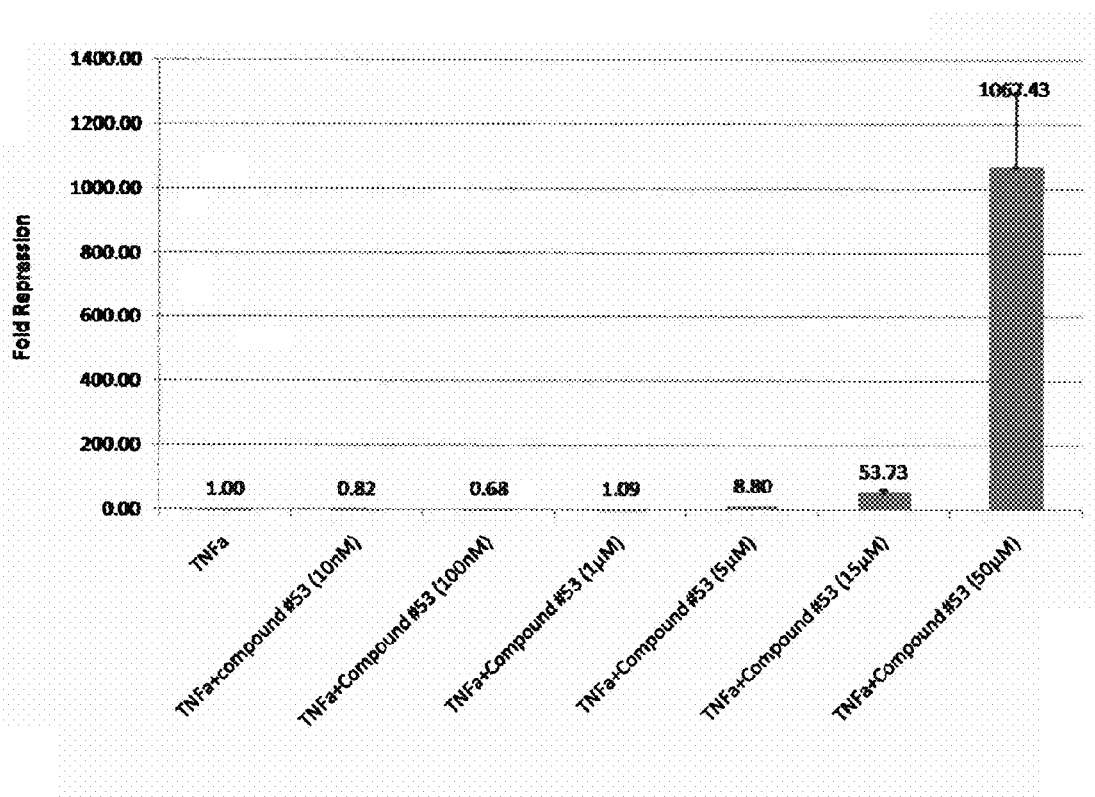
FIG. 10 is a bar graph showing the dose-response of Com-
pound #53 on GR transrepression of NF-kB in AD293 cells.

FIG. 3 shows the structure of Compound #53 bound in the GR ligand binding domain (LBD) as predicted by the molecular docking program GOLD. FIG. 4 shows the 2-dimensional chemical structure of Compound #53 (Example 5 also shows the chemical structure of Compound #53). The inventors' studies show that Compound #53 is an outstanding dissociated GR ligand, with minimal GR transactivation activity (FIG. 5) and stronger GR transrepression activity than currently used GR ligands (FIGS. 6-8). Furthermore, dose-response repression experiments of Compound #53's effect on AP1 and NF-kB shows that with increasing concentrations of Compound #53, the fold repression increases. These studies show that compound #53 blocks AP-1 and NF-kB activity on the reporter in AD293 cells to almost zero. For example, at 50 µM, the fold repression for AP1 is about 2000 and the fold repression of NF-kB is about 1000 (FIGS. 9 and 10, respectively). That is, Compound #53 has impressive GR transrepression properties.

Other compounds of formula I are also expected to have excellent dissociated GR ligand properties. The chemical structures of these other compounds are shown in Examples 6-17. Additional other compounds expected to have excellent dissociated GR ligand properties are described in Table 1, Hintermann, S., et al, *Bioorganic & Medicinal Chemistry Letters*, 17 (2007) 193-196; and U.S. Pat. Nos. 4,086,421; 4,049,813; and 7,087,756; all of which compounds are incorporated into this application by reference.

The present invention also includes a method for treating a subject for arthritis, asthma, lupus, allograft rejection, allergic skin disease, leukemia, multiple sclerosis, inflammatory liver disease, autoimmune hepatitis, inflammatory bowel disease, metabolic disorders, atherosclerosis, brain edema, shock, blood cancer, or adrenal cortex insufficiencies by administering to a subject having arthritis, asthma, lupus, allograft rejection, allergic skin disease, leukemia, multiple sclerosis, inflammatory liver disease, autoimmune hepatitis, inflammatory bowel disease, metabolic disorders, atherosclerosis, brain edema, shock, blood cancer, or adrenal cortex insufficiencies a therapeutically effective amount of the compound of formula I,

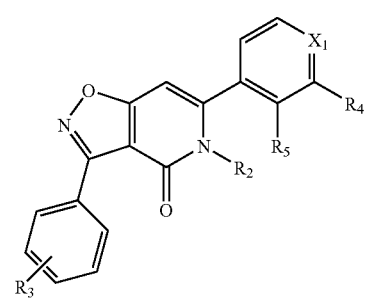

where:
X$_1$ is —N═ and —CR$_1$═;
R$_1$ is —H,
C$_1$-C$_3$ alkyl,
—(CH$_2$)$_x$—N(R$_{1-1}$)(R$_{1-2}$) where x is 0, 1 or 2 and where R$_{1-1}$ and R$_{1-2}$ are the same or different and are —H and C$_1$-C$_3$ alkyl with the proviso that when R$_{1-1}$ and R$_{1-2}$ are both C$_2$ alkyl, the alkyl groups can be cyclized to form a heterocyclic ring selected from the group consisting of pyrrolidinyl, piperidinyl, piperizinyl and N-methylpiperazinyl;
—O—R$_{1-3}$ where R$_{1-3}$ is —H, C$_1$-C$_3$ alkyl and phenyl;
—(CH)$_y$—O—(CH$_2$)$_y$—O—R$_{1-4}$ where y are the same or different and are 1 or 2 and where R$_{1-4}$ is —H, C$_1$-C$_3$ alkyl, —CO—R$_{1-5}$ where R$_{1-5}$ is C$_1$-C$_4$ and phenyl;
R$_2$ is —H, C$_1$-C$_3$ alkyl, and C$_3$ cycloalkyl;
R$_3$ is —H, C$_1$-C$_3$ alkyl, —F, —Cl, —Br and —I;
R$_4$ is —H and —O—R$_{4-1}$ with the proviso that when R$_4$ is —O—R$_{4-1}$, X$_1$ is —R$_1$═ and R$_1$ and R$_4$ are taken together to form a methylenedioxo group;
R$_5$ is —H and —O—R$_{5-1}$ where R$_{5-1}$ is —H, C$_1$-C$_3$ alkyl and phenyl with the proviso that R$_{5-1}$ and R$_{1-3}$ cannot both be phenyl; its enantiomers, diastereomers, tautomers, pharmaceutically acceptable salts and hydrates thereof. In one embodiment, the administered compound is Compound #53.

As used herein the term "treating" means the administration of medicine or the performance of medical procedures with respect to a subject to alleviate or reduce the clinical symptoms or medically measured parameters for a disease/condition to some extent. It may but does not necessarily require curing the disease or condition. For example, if an individual has high blood pressure, treating includes reducing the blood pressure but does not require that the reduction be to normal.

By "therapeutically effective amount" herein is meant an amount of the isoxazolo[4,5-c]pyridine of formula (I) that produces the effect for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)). For example, a therapeutically effective amount may mean an amount sufficient to prevent, or reduce by at least about 25 percent, at least about 50 percent, or at least about 90 percent, a clinically significant change in a feature of pathology such as for example, elevated blood pressure, fever, or white cell count, as may attend its presence and activity. As relates to the present invention, the term may also mean an amount sufficient to prevent, ameliorate or reverse one or more symptoms associated with inflammation or auto-immune disease.

The present method of treatment is administered parenterally, orally, topically (transdermally) or rectally. Parental administration includes intravenous (IV), intramuscular, intradermal, intraperitoneal (IP) or subcutaneously (SQ). Parenteral administration requires a sterile isotonic aqueous solution buffered to an appropriate pH for the selected compound of formula I or a suspension or emulsion for sustained release administration.

The compounds of formula I can be administered orally by solid dosage forms such as tablets, capsules, dispersible granules or lozenges and by liquid dosage forms such as solutions, syrups, suspensions and emulsions. These would include dosages form for immediate release as well as sustained dosage forms for 12 or 24 hour administration.

The compounds of formula I can be administered by way of a transdermal patch which is of particular benefit for those unable to swallow where parenteral administration is not desirable. Further, the compounds of formula I can be formulated into suppositories for rectal administration which is of particular benefit for those unable to swallow where parenteral administration is not desirable. It is known to those skilled in the art how to prepare the sterile parenteral formulations for parenteral administration, solid and liquid dosage forms for oral administrating, transdermal patches and suppositories of the compounds of formula I. The compounds of formula I also can be administered in dosage forms suitable for topical administration including, but not limited to, creams, ointments, lotions, solutions, suspensions, emulsions and bandages impregnated with the selected compound of formula I. It is known to those skilled in the art how to prepare the topical pharmaceutical dosage forms to administer the compounds of formula I.

Parenterally or orally, the selected compound of formula I is given in a therapeutically effective amount to treat a subject for arthritis, asthma, lupus, allograft rejection, allergic skin disease, leukemia, multiple sclerosis, inflammatory liver disease, autoimmune hepatitis, inflammatory bowel disease, metabolic disorders, atherosclerosis, brain edema, shock, blood cancer, or adrenal cortex insufficiencies, which amount is from about 5 to about 100 mg/kg/day. Parenterally, the compounds of formula I are given continuously by way of an IV one to four times daily by injection. When infused IV is used, it should be given at about 60 to 120 ml/hr depending on the concentration of the mixture being administered. Orally, the dose can be given once a day or divided into two or four doses a day. Topically, the topical formulation should have an effective amount of from about 0.05% to 5% of the selected compound of formula I.

The exact dosage and frequency of administration depends on the particular compound of formula I used, the particular condition being treated, the severity of the condition being treated, the age, weight, general physical condition of the particular subject, other medication used by the subject, and/or the subject's response to the particular condition being treated as is known to those skilled in the art. Further, physicians can monitor the progress of treatment by monitoring blood markers as well as the blood level of the compound of formula I as is known to those skilled in the art.

The subject being treated is a warm blooded mammal, including, humans, farm animals such as horses, sheep, cattle, lamas, pigs and the like, as well as pets such as cats and dogs. In one embodiment, the warm blooded mammal is a human.

Having now generally described the invention, the same will be more readily understood through reference to the following examples, which are provided by way of illustration, and are not intended to be limiting of the present invention, unless specified.

EXAMPLES

Example 1

GR Transactivation on MMTV in○AD293 Cells Transfected with 0.5 ng GR. AD293 cells were transfected with 0.5 ng GR, 100 ng pHHLuc reporter together with 5 ng Renilla control plasmids, then induced by EtOH (vehicle control), Dexamethasone (10 nM), Compound #53 (5 µM), AL438 (1 µM) and DMSO (vehicle control). Dual-Luciferase values were measured by Promega standard manual, Compound #53's transactivation activity on MMTV in AD293 cells is shown in FIG. 5.

Example 2

GR Transrepression of AP1 in AD293 Cells Transfected with 10 ng GR. AD293 cells were transfected with 10 ng GR, 100 ng AP1-Luc reporter together with 5 ng Renilla control plasmids, then induced by EtOH (vehicle control), Dexamethasone (10 nM), Compound #53 (5 µM), AL438 (1 µM). Dual-Luciferase values were measured by Promega standard manual. Compound #53's GR transrepression activity on AP1 in AD293 cells is shown in FIG. 6.

Example 3

GR Transpression of AP 1 in AD293 Cells Transfected with 50 ng GR. AD293 cells were transfected with 50 ng GR, 100 ng AP1-Luc reporter together with 5 ng Renilla control plasmids, then induced by PMA+EtOH (vehicle control), PMA+Dexamethasone (10 nM), PMA+Compound #53 (5 µM). Dual-Luciferase values were measured by Promega standard manual. Compound #53's GR transrepression activity on AP1 in AD293 cells is shown in FIG. 7.

Example 4

GR Transrepression of NF-kB in AD293 Cells Transfected with 100 ng GR. AD293 cells were transfected with 100 ng GR, 100 ng pNF-kB-Luc reporter together with 5 ng Renilla control plasmids, then induced by TNFa+EtOH (vehicle control), TNFa+Dexamethasone (1 µM), TNFa+Compound #53 (5 µM), TNFa+DMSO. Dual-Luciferase values were measured by Promega standard manual. Compound #53's GR transrepression activity on NF-kB in AD293 cells is shown in FIG. 8.

Example 5

6-(4-((dimethylamino)methyl)phenyl)-5-methyl-3-phenylisoxazolo[4,5-c]pyridin-4(5H)-one [CAS no: 64769-68-2, referred to herein as "Compound #53"]

(I)

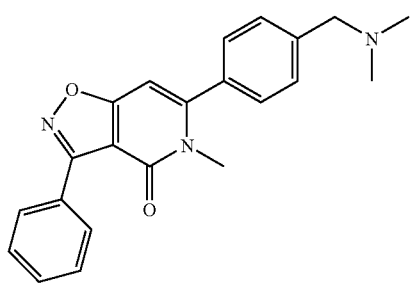

Example 6

6-(4-((dimethylamino)methyl)phenyl)-3-(4-fluorophenyl)-5-methylisoxazolo[4,5-c]pyridin-4(5H)-one (I)

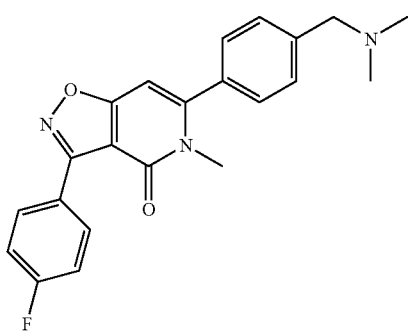

Example 7

6-(4-diethylamino-phenyl)-5-methyl-3-phenyl-5H-isoxazolo[4,5-c]pyridin-4-one [CAS no. 479077-27-5] (I)

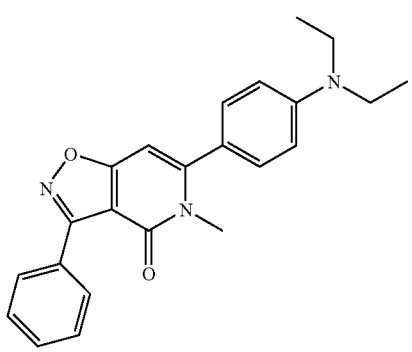

Example 8

6-(4-methoxyphenyl)-5-methyl-3-phenylisoxazolo[4,5-c]pyridin-4(5H)-one [CAS no: 60986-85-8] (I)

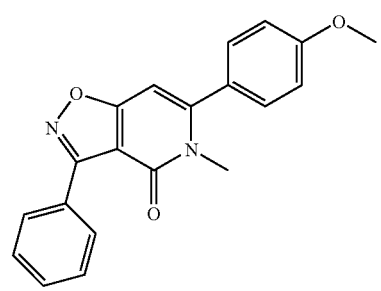

Example 9

6-(2,4-dimethoxyphenyl)-5-methyl-3-phenylisoxazolo[4,5-c]pyridin-4(5H)-one [CAS no: 500164-93-2] (I)

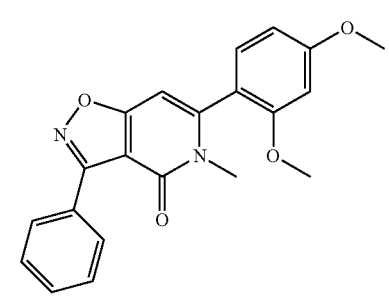

Example 10

6-(benzo[d][1,3]dioxol-5-yl)-5-methyl-3-phenylisoxazolo[4,5-c]pyridin-4(5H)-one [CAS no: 479077-19-5] (I)

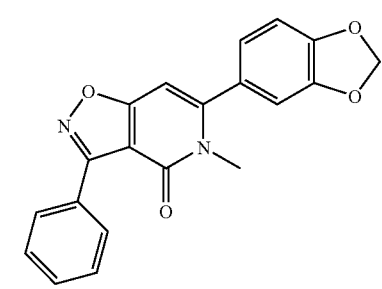

Example 11

6-(4((2-hydroxyethoxy)methyl)phenyl)-5-methyl-3-phenylisoxazolo[4,5-c]pyridin-4(5H)-one [CAS no. 500165-01-5] (I)

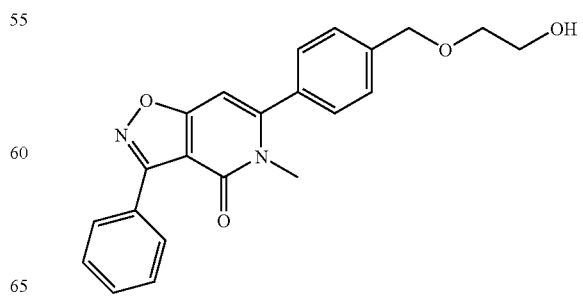

Example 12

6-(4((2-methoxyethoxy)methyl)phenyl)-5-methyl-3-phenylisoxazolo[4,5-c]pyridin-4(5H)-one [CAS no. 500164-74-9] (I)

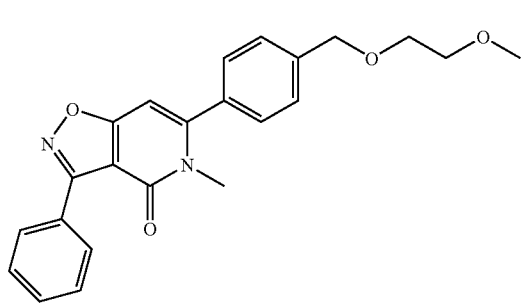

Example 13

6-(4-((2-isopropoxyethoxy)methyl)phenyl)-5-methyl-3-phenylisoxazolo[4,5-c]pyridin-4(5H)-one [CAS no. 920984-07-2] (I)

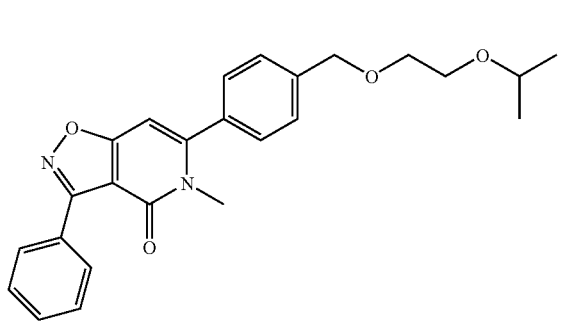

Example 14

5-methyl-6-(4-phenoxyphenyl)-3-phenyl-isoxazolo[4,5-c]pyridin-4(5H)-one [CAS no. 500164-73-8] (I)

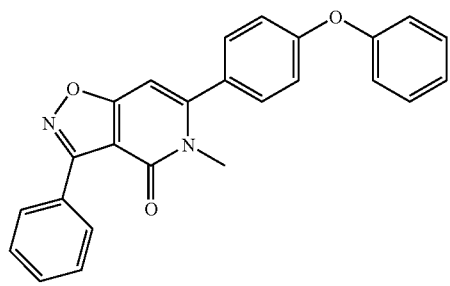

Example 15

5-methyl-6-(4((4-methylpiperazin-1-yl)methyl)phenyl)-3-phenylisoxazolo[4,5-c]pyridin-4(5H)-one [CAS no. 500164-70-5] (I)

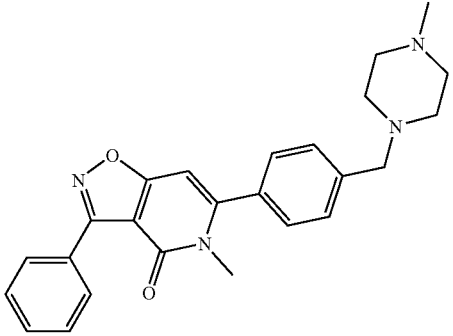

Example 16

5-methyl-3-phenyl-6-(pyridin-4-yl)isoxazolo[4,5-c]pyridin-4(5H)-one [CAS no: 479077-12-8] (I)

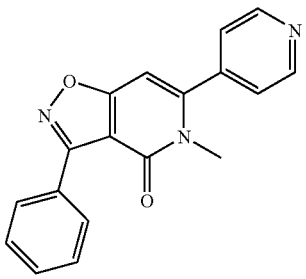

Example 17

5-methyl-3-phenyl-6-p-tolylisoxazolo[4,5-c]pyridin-4(5H)-one [CAS no: 60986-84-7] (I)

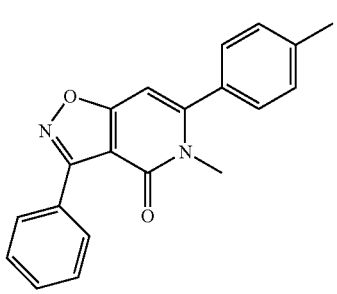

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. A method of treating a disease selected from the group consisting of arthritis and asthma in warm blooded mammals which comprises administering a therapeutically effective amount of an isoxazolo[4,5-c]pyridine of formula (I)

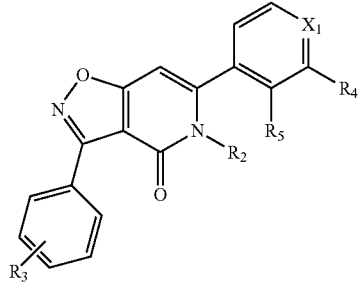

where:
$X_1$ is —N= or —$CR_1$=, wherein
$R_1$ is

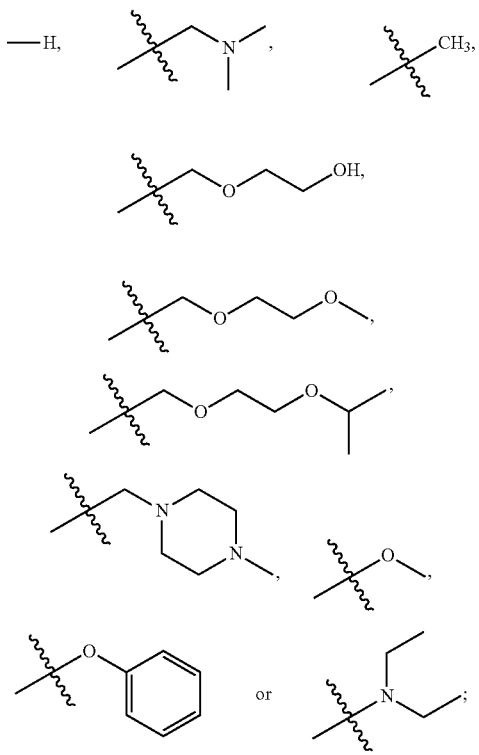

$R_2$ is methyl;
$R_3$ is —H or F;
$R_4$ is —H; or $R_1$ and $R_4$ together with the carbon atoms to which they are attached form the moiety

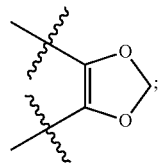

$R_5$ is —H or methoxy; enantiomers, diastereomers, tautomers and pharmaceutically acceptable salts thereof.

2. The method according to claim 1 where the warm blooded mammal is a human.

3. The method according to claim 1 where the effective amount is from about 1 to about 100 mg/kg/day.

4. The method according to claim 3 where the effective amount is from about 5 to about 50 mg/kg/day.

5. The method according to claim 1 where the isoxazolo [4,5-c]pyridine (I) is selected from the group consisting of
6-(4-((dimethylamino)methyl)phenyl)-5-methyl-3-phenylisoxazolo[4,5-c]pyridin-4(5H)-one,
6-(4-((dimethylamino)methyl)phenyl)-3-(4-fluorophenyl)-5methylisoxazolo[4,5-c]pyridin-4(5H)-one,
6-(4-diethylamino-phenyl)-5-methyl-3-phenyl-5H-isoxazolo[4,5c]pyridin-4-one,
6-(4-methoxyphenyl)-5-methyl-3-phenylisoxazolo[4,5-c]pyridin-4(5H)-one,
6-(2,4-dimethoxyphenyl)-5-methyl-3-phenylisoxazolo[4,5-c]pyridin-4(5H)-one,
6-(benzo[d][1,3]dioxol-5-yl)-5-methyl-3-phenylisoxazolo[4,5c]pyridin-4(5H)-one,
6-(4-((2-hydroxyethoxy)methyl)phenyl)-5-methyl-3-phenylisoxazolo[4,5-c]pyridin-4(5H)-one,
6-(4-((2-methoxyethoxy)methyl)phenyl)-5-methyl-3phenylisoxazolo[4,5-c]pyridin-4(5H)-one,
6-(4-((2-isopropoxyethoxy)methyl)phenyl)-5-methyl-3phenylisoxazolo[4,5-c]pyridin-4(5H)-one,
5-methyl-6-(4-phenoxyphenyl)-3-phenyl-isoxazolo[4,5-c]pyridin-4(5H)-one,
5-methyl-6-(4-((4-methylpiperazin-1-yl)methyl)phenyl)-3phenylisoxazolo[4,5-c]pyridin-4(5H)-one,
5-methyl-3-phenyl-6-(pyridin-4-yl)isoxazolo[4,5-c]pyridin-4(5H)-one, and
5-methyl-3-phenyl-6-p-tolylisoxazolo[4,5-c]pyridin-4(5H)-one.

6. The method according to claim 5 where the isoxazolo [4,5-c]pyridine (I) is 6-(4-((dimethylamino)methyl)phenyl)-5-methyl-3phenylisoxazolo[4,5-c]pyridin-4(5H)-one.

7. A method for retaining or increasing glucocorticoid receptor transrepression activity in a cell with only minimal glucocorticoid receptor transactivation activity comprising administering to a cell which needs modification a usable amount of an isoxazolo[4,5-c]pyridine of formula (I)

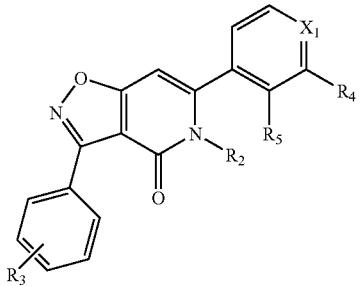

(I)

where:

X₁ is —N═ or —CR₁═, wherein
R₁ is

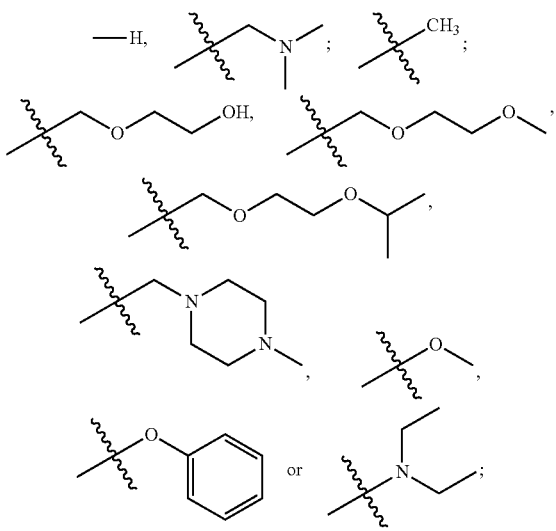

R₂ is methyl;
R₃ is —H or F;
R₄ is H; or R₁ and R₄ together with the carbon atoms to which they are attached form the moiety

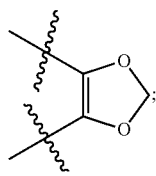

$R_5$ is —H or methoxy; enantiomers, diastereomers, tautomers and pharmaceutically acceptable salts thereof.

8. The method according to claim 7 where the isoxazolo[4,5-c]pyridine (I) is selected from the group consisting of
6-(4-((dimethylamino)methyl)phenyl)-5-methyl-3-phenylisoxazolo[4,5-c]pyridin-4(5H)-one,
6-(4-((dimethylamino)methyl)phenyl)-3-(4-fluorophenyl)-5methylisoxazolo[4,5-c]pyridin-4(5H)-one,
6-(4-diethylamino-phenyl)-5-methyl-3-phenyl-5H-isoxazolo[4,5c]pyridin-4-one,
6-(4-methoxyphenyl)-5-methyl-3-phenylisoxazolo[4,5-c]pyridin-4(5H)-one,
6-(2,4-dimethoxyphenyl)-5-methyl-3-phenylisoxazolo[4,5-c]pyridin-4(5H)-one,
6-(benzo[d][1,3]dioxol-5-yl)-5-methyl-3-phenylisoxazolo[4,5c]pyridin-4(5H)-one,
6-(4-((2-hydroxyethoxy)methyl)phenyl)-5-methyl-3-phenylisoxazolo[4,5-c]pyridin-4(5H)-one,
6-(4-((2-methoxyethoxy)methyl)phenyl)-5-methyl-3phenylisoxazolo[4,5-c]pyridin-4(5H)-one,
6-(4-((2-isopropoxyethoxy)methyl)phenyl)-5-methyl-3phenylisoxazolo[4,5-c]pyridin-4(5H)-one,
5-methyl-6-(4-phenoxyphenyl)-3-phenyl-isoxazolo[4,5-c]pyridin-4(5H)-one,
5-methyl-6-(4-((4-methylpiperazin-1-yl)methyl)phenyl)-3phenylisoxazolo[4,5-c]pyridin-4(5H)-one,
5-methyl-3-phenyl-6-(pyridin-4-yl)isoxazolo[4,5-c]pyridin-4(5H)one and
5-methyl-3-phenyl-6-p-tolylisoxazolo[4,5-c]pyridin-4(5H)-one.

9. The method according to claim 8 where the isoxazolo[4,5-c]pyridine (I) is 6-(4-((dimethylamino)methyl)phenyl)-5-methyl-3phenylisoxazolo[4,5-c]pyridin-4(5H)-one.

* * * * *